United States Patent [19]

Uemura et al.

[11] Patent Number: 5,290,228
[45] Date of Patent: Mar. 1, 1994

[54] TWO-COMPARTMENT SYRINGE

[75] Inventors: Osamu Uemura, Suita; Yukio Kusu, Ibaraki, both of Japan

[73] Assignee: Santen Seiyaku Kabushiki Kaisha, Osaka, Japan

[21] Appl. No.: 910,281

[22] PCT Filed: Nov. 18, 1991

[86] PCT No.: PCT/JP91/01575
§ 371 Date: Jul. 16, 1992
§ 102(e) Date: Jul. 16, 1992

[87] PCT Pub. No.: WO92/08504
PCT Pub. Date: May 29, 1992

[30] Foreign Application Priority Data

Nov. 17, 1990 [JP] Japan .................. 2-120389[U]
Nov. 19, 1990 [JP] Japan .................. 2-121461[U]
Jan. 31, 1991 [JP] Japan .................. 3-10399

[51] Int. Cl.5 .................................... A61M 5/19
[52] U.S. Cl. .................................... 604/90; 604/220; 604/227; 604/230
[58] Field of Search ............. 604/82, 87, 89, 92, 604/187, 201, 205, 218, 220, 221, 225, 227, 230, 231, 236

[56] References Cited

U.S. PATENT DOCUMENTS

| 3,316,909 | 5/1967 | Cowley | 604/227 |
| 3,388,941 | 6/1968 | Marcus | 604/227 |
| 3,640,278 | 2/1972 | Friedman | 604/227 |
| 4,060,083 | 11/1977 | Hanson | 604/227 |
| 4,767,414 | 8/1988 | Williams et al. | 604/230 |
| 4,874,381 | 10/1989 | Vetter | 604/91 |

FOREIGN PATENT DOCUMENTS 180538 12/1980 Japan .
2-36881 6/1990 Japan .

*Primary Examiner*—John D. Yasko
*Assistant Examiner*—Anthony Gutowski
*Attorney, Agent, or Firm*—Webb, Burden, Ziesenheim & Webb

[57] ABSTRACT

The present invention is a two-compartment syringe which may contain a medical substance, such as a freeze-dried powder, and a solvent separately. When used, the medical substance and solvent are mixed for injection. A silicone coating is used inside the syringe barrel. The syringe is further provided with finger hooks to enable use of the syringe with one hand.

10 Claims, 7 Drawing Sheets

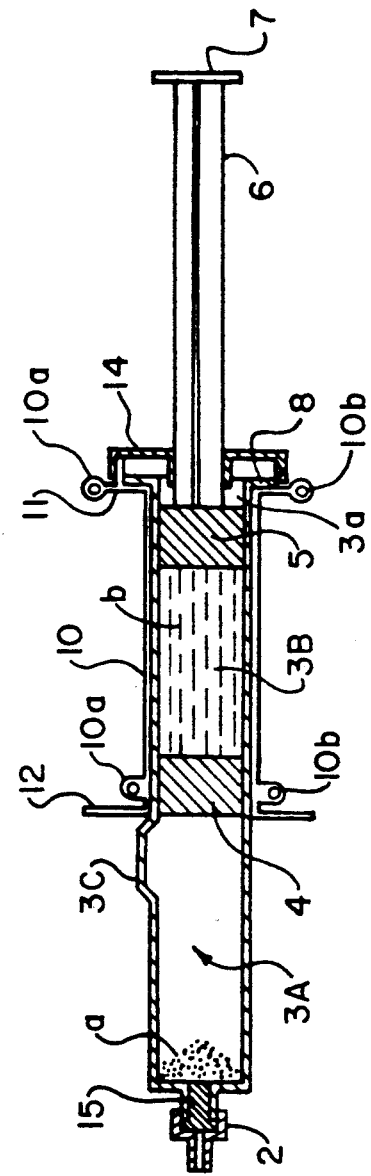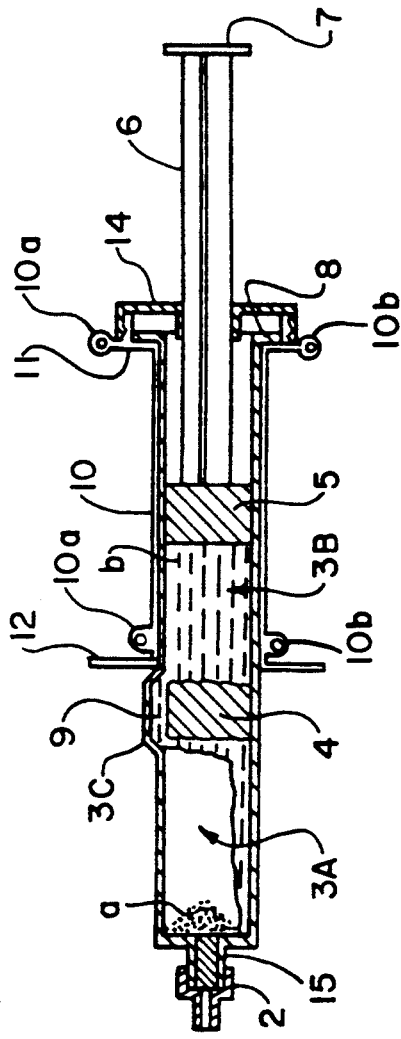

TWO-COMPARTMENT SYRINGE

TECHNICAL FIELD

The present invention relates to a two-compartment syringe, and more particularly to a two-compartment syringe wherein freeze-dried powder and solvent are contained in a separate state in the syringe. In use, the freeze-dried powder and solvent are mixed for injection.

BACKGROUND ART

There are various dosage forms for medicines. In the case of aqueous preparations such as injections, it is desirable to put them in the form of solution, which is a final form, at a time of preparation. However, not a few medical substances are unstable in dissolved state. Therefore, such medical substances are generally dissolved at a time of use and applied, that is a dissolving method in use. Further, some medical substances cannot be obtained in crystals or are highly hygroscopic. In such cases, the medical substances are often practically used in the form of freeze-dried powder. In the case of injections, for example, a method is generally used in which freeze-dried powder is placed in a vial bottle or the like, dissolved by putting a solvent thereinto, and drawn up through an injection needle. However, it is more convenient to contain the solvent and freeze-dried powder in a syringe from the beginning. For use in a surgical operation, it is necessary to take maintenance of sterilized condition into consideration particularly.

Methods have been proposed in which a medical substance and solvent are contained in a syringe from the beginning, and dissolution is effected within the syringe immediately before use. Specifically, in such methods, a medical substance in the form of freeze-dried powder or the like is placed in the bottom of a syringe adjacent an injection needle connecting portion, and a solvent for the medical substance is placed in a plunger rod attaching portion of the syringe. The medical substance containing chamber and solvent containing chamber are partitioned in an appropriate way. The solvent and medical substance are mixed in an appropriate way for dissolution at a time of use (Japanese Patent Publication No. 50-4992, Japanese Patent Publication Kokai No. 60-72561, Japanese Utility Model Publication No. 49-14465).

However, freeze-dried powder tends to be charged with static electricity and often is in a trace quantity. Therefore, it is not easy to place the powder in the syringe accurately. In order to improve such drawbacks, it is conceivable to carry out freeze-drying in the syringe. Usually the syringe has an inner wall coated with a silicone oil solution having a concentration of 1-5% (W/V) in order to enable smooth movement of gaskets and a plunger rod in use. A solution of medicine becomes turbid when freeze-dried after placement in a silicone-coated syringe in the above concentration and then redissolved as a freeze-dried powder in a solvent. The product is then not suitable as a medicine.

On the other hand, in a known form of such a two-compartment syringe, gaskets are used to partition between the powder containing chamber and solvent containing chamber and between the solvent containing chamber and ambient air, respectively, as in the publications noted above. However, there is a risk that expansion of interior air in the powder containing chamber is caused by an increase of temperature, and pushes up the gaskets, whereby the gaskets fall off. A syringe is also known which includes a flange-like finger hook formed integral with an outer peripheral surface thereof for pushing in the plunger rod to mix the powder and solvent and to push the solution out of the syringe.

However, a two-step operation is necessary with a two-compartment syringe, and there has been a problem in securely supporting the syringe to give an injection to an affected organ exactly.

The objects of the present invention are to provide a two-compartment syringe capable of suppressing turbidity occurring when freeze-dried powder is dissolved in a solvent to a degree not obstructive to use while maintaining movement of the gaskets and plunger rod in a smooth condition with silicone coating applied to the inner wall of the syringe. A further object of the present invention is to provide a two-compartment syringe having excellent operability and devised to be capable of preventing the gaskets from falling off caused by air expansion in the powder containing chamber and capable of mixing the powder and solvent. Another object is to provide a syringe for injecting the resulting liquid mixture easily and accurately.

DISCLOSURE OF THE INVENTION

In order to achieve the above objects, a characteristic construction of the present invention lies in a two-compartment syringe having freeze-dried powder obtained by freeze-drying a solution of medicine in a syringe inverted with a needle connecting side disposed below and contained in a bottom of the syringe barrel, a containing space for this freeze-dried powder partitioned by an elastic first gasket inserted into the syringe barrel, a solvent for the freeze-dried powder stored between the first gasket and an elastic second gasket inserted into the barrel, and a plunger rod attached to the second gasket.

The two-compartment syringe includes coating layers formed on an inner wall of the syringe barrel contacted by the solution of medicine to be freeze-dried, by coating with a silicone oil solution having a concentration not exceeding 0.3% (W/V), and on an inner wall of the syringe barrel substantially out of contact with the solution of medicine, by coating with a silicone oil solution having a concentration of at least 1% (W/V).

A further characteristic construction of the present invention lies in that the syringe has a stopper disposed at an opening side thereof for contacting, in an axial direction of the syringe, the plunger rod or the gasket disposed adjacent an opening of the syringe to prevent the gasket from falling off.

The syringe has a first finger hook disposed at an opening end thereof and projecting diametrically outwardly of the syringe, and a second finger hook disposed on an intermediate portion of the syringe barrel displaced from the first finger hook toward the needle connecting side and projecting diametrically outwardly of the syringe.

The functions and effects will be described next.

Various studies have been made to find the cause of turbidity occurring when the freeze-dried powder is dissolved in the solvent, and it has been found as a result that the turbidity is caused by the silicone coating. Then, the inventors have conducted intensive research for silicone coating concentrations not causing turbidity. A relationship between concentration and turbidity of the silicone oil solution and sliding force obtained through an experiment carried out in the course of the research is shown in Table 1 noted hereinafter. As seen from the results of the experiment, it has been found that substantially no turbidity occurs where the silicone coating has a concentration not exceeding 0.3% (W/V) (% by weight per volume). Further, it has been found that movement of the gasket and plunger rod is substantially little affected by a lowered concentration of the silicone coating for the chamber accommodating the solution of medicine to be freeze-dried, i.e. the inner wall portion of the syringe barrel contacted by the solution of medicine.

Thus, a two-compartment syringe is provided in which the silicone coating concentration of the coating layers applied to the inner walls of the syringe barrel is differentiated as above to be capable of suppressing the turbidity occurring when the freeze-dried powder obtained by freeze-drying the solution of medicine in the syringe is dissolved in the solvent in the syringe for use, to a degree not obstructive to use, while maintaining movement of the gasket and plunger rod in a smooth condition.

On the other hand, when air in the powder containing chamber, one of the two chambers in the syringe partitioned by the two gaskets, expands by a rise in ambient temperature, and a pressure acts on the gasket disposed adjacent the opening of the syringe in the fall-off direction. This gasket may be prevented from falling off by contact with the retaining stopper attached to the opening end of the syringe.

Moreover, this stopper contacts, in the axial direction of the syringe, the plunger rod or the gasket disposed at the opening side of the syringe, and therefore presents no obstacle to an operation to push in the plunger rod.

Thus, it is now possible to prevent the gasket and plunger rod from falling off the syringe caused by a rise in ambient temperature while facilitating operation of the plunger rod at a time of injection.

Where the stopper defines a guide for guiding movement of the plunger rod axially of the syringe, the plunger rod may advantageously be pushed in smoothly without wobbles.

On the other hand, the arrangement of two finger hooks produces the following functions and effects.

When pushing in the plunger rod (upon start of an injection), the top of the plunger rod is pushed in with a thumb, with a middle finger and an index finger engaging the first finger hook disposed at the opening side of the syringe. Before support of the syringe becomes unstable in the course of the push-in operation of the plunger rod, the fingers are switched to the second finger hook disposed in the intermediate portion of the syringe barrel. The plunger rod is pushed in further, hooking the second finger hook as a supporting point of the operation.

Thus, by switching the fingers from the first finger hook to the second finger hook during injection, the distance between the finger hook and the thumb rest at the top of the plunger rod may be maintained within a range enabling stable support for the syringe. Even where the syringe having a long axial barrel as in the case of a syringe for two components, for example, a stable operation may be attained from beginning to end of the injection.

Where the two finger hooks are formed integral with a holder detachably mounted on the syringe, such holder may readily be assembled with a ready-made syringe and a practical advantage of low manufacturing cost is provided in that they may be produced independently of the syringe for which a relatively high shaping precision is required.

BRIEF DESCRIPTION OF THE DRAWINGS

FIG. 1 is a sectional side view showing a two-compartment syringe according to the present invention, FIG. 2 is a sectional side view showing freeze-dried powder and solvent halfway through a mixing process.

BEST MODE FOR CARRYING OUT THE INVENTION

A two-compartment syringe embodying the present invention will be described in detail hereinafter with reference to the drawings.

Figure 3:
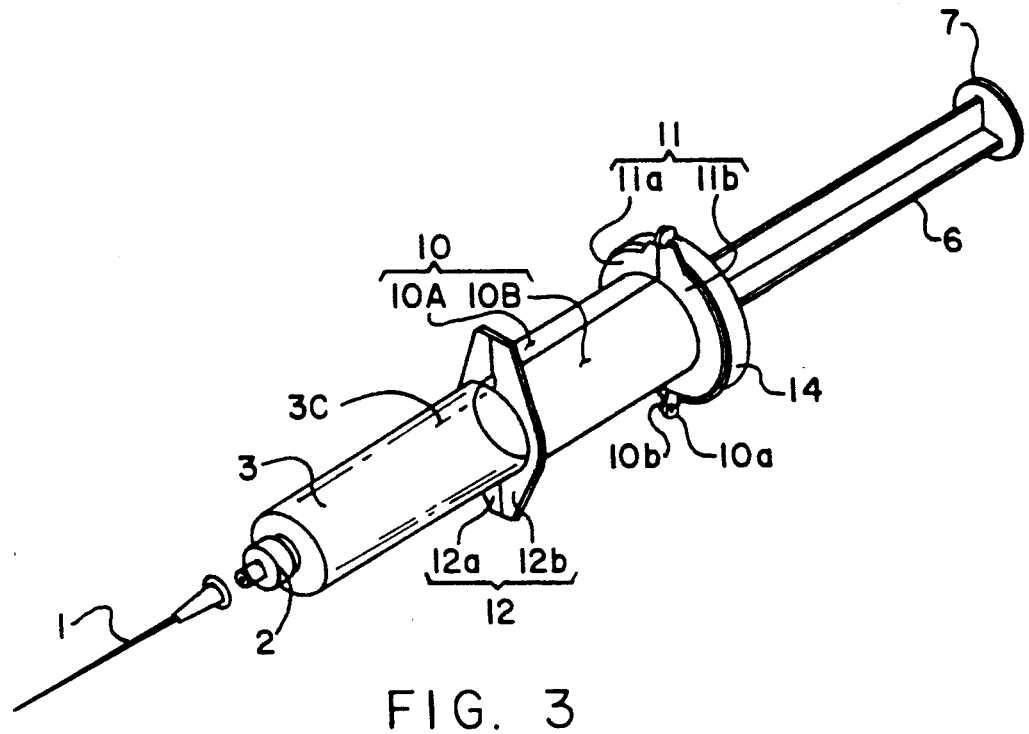
FIG. 3 is a perspective overall view.
Figure 4:
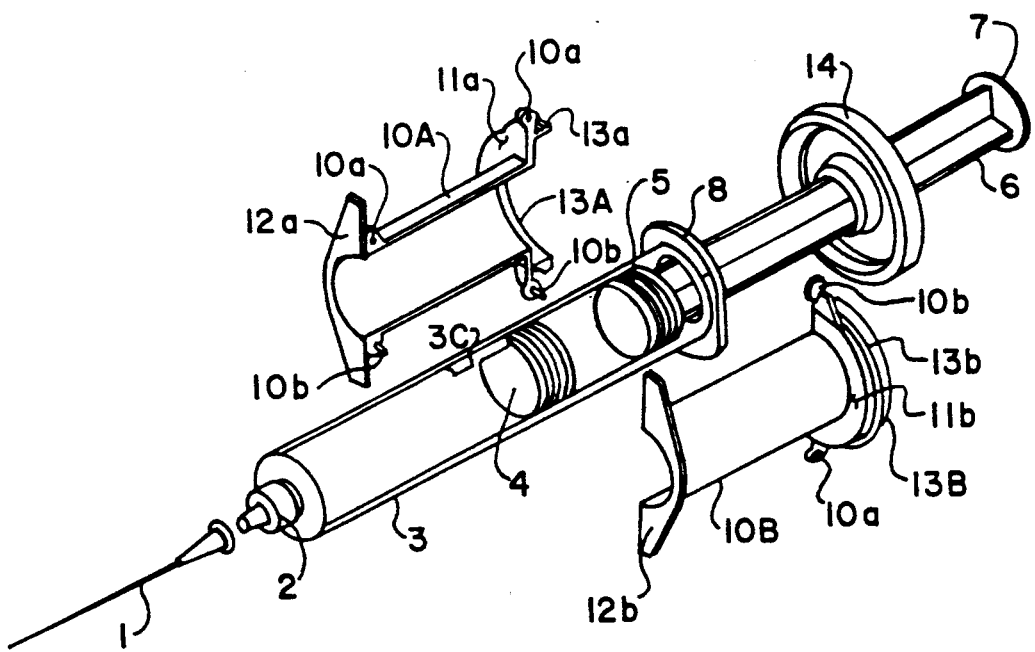
FIG. 4 is an exploded perspective overall view, FIGS. 5(a) and (b) are explanatory views showing Specific Example 1 of a silicone coating treatment method, FIGS. 6(a) and (b) are explanatory views showing Specific Example 2 of the silicone coating treatment method.

FIGS. 1 and 2 show a two-compartment syringe in one embodiment of the present invention, and FIGS. 3 and 4 show an injector having the above two-compartment syringe. A cylindrical syringe 3 having a needle connecting side 2 for connecting a needle 1 includes two elastic, first gasket 4 and second gasket 5 slidably inserted therein through an opening 3a formed at the other end of this syringe 3.

The first gasket 4 and second gasket 5 are formed of cylindrical halogenobutyl rubber having a diameter slightly larger than inside diameter of the syringe barrel 3, and provide fluid-tight seals with the inner wall of the syringe barrel 3 upon insertion into the syringe 3.

Of two chambers 3A and 3B partitioned in fluid-tight condition by the first gasket 4 and second gasket 5, the first chamber 3A disposed adjacent the needle connecting side 2 contains freeze-dried powder "a" obtained by freeze-drying a solution of medicine inside the syringe 3 in an inverted posture with the needle connecting side 2 lying below. On the other hand, the second chamber 3B disposed adjacent the opening 3a contains a solvent "b" for dissolving the freeze-dried powder "a".

The second gasket 5 disposed adjacent the opening 3a of the syringe 3 has a plunger rod 6 detachably screwed tight thereto for sliding the second gasket 5 axially of the syringe 3. The plunger rod 6 has a thumb rest 7 formed at the top thereof and having a flatter shape larger than the inside diameter of the syringe barrel 3.

The syringe 3 includes a flange 8 projecting diametrically outwardly from an outer peripheral surface thereof at the end where the opening 3a is formed. Further, the syringe 3 includes a ridge 3C formed in an axially intermediate position thereof and bulging radially outwardly. A bypass passage 9 is provided inside the ridge 3C for intercommunicating the first chamber 3A and second chamber 3B of the syringe 3.

This bypass passage 9 has a length axially of the syringe barrel which is slightly greater than an axial length of the first gasket 4 disposed adjacent the needle connecting side 2. When, as shown in FIG. 2, the first gasket 4 lies in the region of the bypass passage 9 during an operation to push in the plunger rod 6, the solvent "b" in the second chamber 3B is led into the first chamber 3A through the bypass passage 9.

On the outer peripheral surface of the syringe 3, the syringe barrel between the flange 8 and ridge 3C has a plastic holder 10 detachably attached thereto.

This holder 10 is divided into two parts by an imaginary plane extending through the axis of the syringe barrel 3. Female and male connectors 10a and 10b for elastically fitting to each other diametrically of the syringe 3 are formed integral with mating surfaces of the two split holder parts 10A and 10B at two positions of each of the ends thereof adjacent the opening 3a of the syringe 3 and the ends adjacent the needle connecting side 2.

A first finger hook 11 having a pair of supporting pieces 11a and 11b projecting diametrically outwardly of the flange 8 is formed integral with the ends of the split holder parts 10A and 10B of the holder 10 adjacent the opening 3a of the syringe 3. On the other hand, a second finger hook 12 having a pair of supporting pieces 12a and 12b exhibiting the same shape as the supporting pieces 11a and 11b of the first finger hook 11 when seen axially of the syringe is formed integral with the ends adjacent the needle connecting side 2.

The supporting pieces 11a and 11b of the first finger hook 11 have a pair of half cylinders 13A and 13B formed integral with end faces thereof lying adjacent the opening 3a of the syringe 3, for surrounding the flange 8. Further, a plastic retaining stopper 14 mounted on the plunger rod 6 is detachably fitted in the axial direction of the syringe to these two half cylinders 13A and 13B. The stopper 14 provided as above can prevent the gasket disposed adjacent the syringe opening from falling off when this gasket is subjected to a pressure acting in the fall-off direction as a result of a rise in ambient temperature to increase the pressure in the dried medicine containing chamber of the two chambers of the syringe partitioned by the two gaskets.

Moreover, this stopper contacting, in the axial direction of the syringe, the plunger rod or the gasket disposed adjacent the syringe opening presents no obstacle to the operation to push in the plunger rod.

Thus, compared with the known screw type injectors, this injector is convenient in that the gasket and plunger rod are positively prevented from falling off the syringe caused by a rise in ambient temperature while facilitating operation of the plunger rod at a time of injection.

A plug 15 of halogenobutyl rubber is mounted in a bore formed in the needle connecting side 2 of the syringe 3, which is perforated by the needle 1 attached to the needle connecting side 2.

In the two-compartment syringe constructed as above, the inner wall of the syringe barrel 3 contacted by the solution of medicine to be freeze-dried has a coating layer formed by a coating treatment with a silicone oil solution having a concentration not exceeding 0.3% (W/V). On the other hand, the inner wall of the syringe barrel 3 substantially free from contact with the solution of medicine has a coating layer formed by a coating treatment with a silicone oil solution having a concentration of at least 1% (W/V).

The silicone oil solutions are prepared by dissolving silicone oil in desired concentrations in a highly volatile liquefied gas of chlorofluorocarbon (flon) or the like.

While specific examples of coating treatment method will be described later, in a common method of manufacturing the syringe 3 of the present invention, the entire inner wall of the syringe barrel 3 is first coated with a silicone oil solution having a concentration not exceeding 0.3% (W/V), and then the inner wall of the syringe barrel 3 outside the part containing the solution of medicine is coated with a silicone oil solution having a concentration of at least 1% (W/V). It is of course possible to coat only the inner wall of the syringe barrel 3 containing the solution of medicine with the silicone oil solution having a concentration not exceeding 0.3% (W/V) and thereafter to coat the inner wall of the syringe barrel 3 outside the part containing the solution of medicine with the silicone oil solution having a concentration of at least 1% (W/V). However, the former is more convenient.

Examples of the coating methods are a method in which the silicone oil solutions are sprayed, a method in which the solutions are drawn through the bore formed in the needle connecting side 2 of the syringe 3, and a method in which the syringe 3 is immersed in tanks of the silicone oil solutions, but not to be limited to the above methods.

While the area for coating the silicone oil solution having a concentration not exceeding 0.3% (W/V) is the inner wall of the syringe barrel 3 contacted by the solution of medicine to be freeze-dried, a coating area may be slightly smaller than a surface area of the inner wall of the syringe barrel 3 contacted by the solution of medicine to be freeze-dried as long as the turbidity occurring at a time of dissolution inside the syringe 3 of the freeze-dried powder "a" obtained by freeze-drying the solution of medicine inside the syringe 3 and the solvent "b" presents no obstacle in use. In practice, it is desirable that the inner wall including the part to which the solution of medicine may splash is coated with the silicone oil solution having a concentration not exceeding 0.3% (W/V).

The syringe 3 thus obtained is inverted with the needle connecting side 2 disposed below where the rubber plug 15 is inserted into and seals the bore of the needle connecting side 2, and the solution of medicine is placed and freeze-dried in the syringe 3. Next, the first gasket 4 is inserted into the syringe barrel 3, thereafter the solvent "b" is placed, and the upper end is sealed tight with the second gasket 5. In use, the plunger rod 6 is attached to the second gasket 5, and the needle 1 is attached to the needle connecting side 2 of the syringe 3. The plunger rod 6 may of course be attached to the second gasket 5 at the beginning.

Specific examples of the coating treatment method will be described next.

SPECIFIC EXAMPLE 1

Figure 5A:
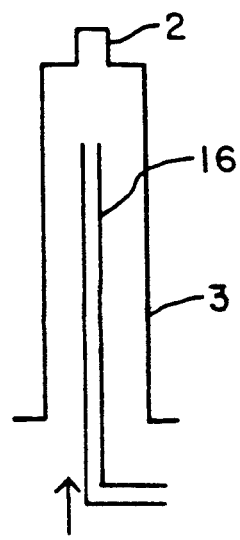
Figure 5B:
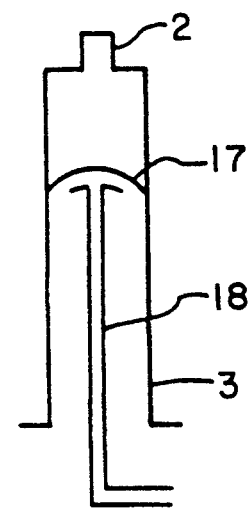

As shown in FIGS. 5(a) and (b), the syringe 3 is inverted with the needle connecting side 2 disposed above, and a silicone oil solution having a concentration of 0.1% (W/V) [a solution prepared by dissolving silicone oil (SH-200 manufactured by Toray-Dow Corning) in Flon 113 (CCl$_2$F—CClF$_2$: Freon TF manufactured by Mitsui Dupont Fluorochemical)] is sprayed through a nozzle 16 inserted through the opening 3a in this state. Next, a nozzle 18 carrying a partition at a top thereof is inserted through the opening 3a of the syringe 3 so that the solution will not spread to the portion contacted by the solution of medicine to be freeze-dried, and a silicone oil solution having a concentration of 3% (W/V) (prepared in the same way as the 0.1% solution) is applied to the inner wall of the syringe barrel 3 substantially free from contact with the solution of medicine, which is followed by a drying treatment.

SPECIFIC EXAMPLE 2

Figure 6A:
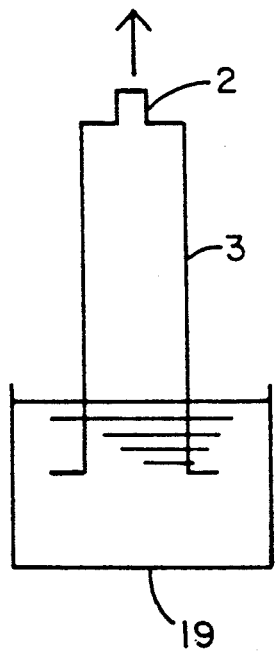
Figure 6B:
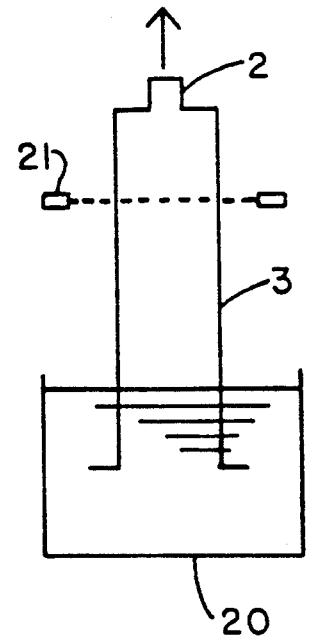

As shown in FIGS. 6 (a) and (b), the syringe 3 is inverted with the needle connecting side 2 disposed above, and immersed slightly in a tank 19 containing a silicone oil solution having a concentration of 0.1% (W/V) (prepared in the same way as in Specific Example 1 above). The silicone oil solution in the tank 19 is drawn up to the needle connecting side 2 of the syringe 3 by applying suction through the bore formed in the needle connecting side 2 of the syringe 3. Next, the tank 19 is replaced by a tank 20 containing a silicone oil solution having a concentration of 3% (W/V) (prepared in the same way as in Specific Example 1 above). The syringe 3 is again immersed slightly therein in the inverted posture with the needle connecting side 2 disposed above, and thereafter suction is applied through the needle connecting side 2 of the syringe 3. At this time, the silicone oil solution in the tank 20 is drawn up to a position just short of the section contacted by the solution of medicine to be freeze-dried, while detecting the draw-up position by means of an optical sensor 21. Thereafter the syringe 3 is removed from the tank 20 for a drying treatment.

Next, the inventor carried out an experiment to show a relationship among concentration of a silicone oil solution, turbidity and sliding force.

In this experiment, a 10% aqueous solution of mannitol was used as an example of solution of medicine to be freeze-dried, and purified water as an example of solvent.

The needle connecting sides 2 of the syringes 3 manufactured by the above two specific method examples were sealed tight with rubber covers, the syringes 3 were inverted with the needle connecting sides 2 disposed below, and the 10% aqueous solution of mannitol was placed and freeze-dried therein. Then, the first gaskets 4 of halogenobutyl rubber were inserted into the syringes 3, and after placing purified water therein, the second gaskets 5 of halogenobutyl rubber were mounted in place. Syringes containing the 10% aqueous solution of mannitol and purified water were prepared in this way.

Then, observation was made of degrees of turbidity occurring when the freeze-dried powder of the 10% aqueous solution of mannitol was dissolved in the purified water, and resistance (sliding force) occurred when the plunger rod 6 was pushed down. Results of the experiment are shown in Table 1.

In Table 1, "−" in the degrees of turbidity shows that no turbidity occurred, "+" shows occurrence of turbidity, and "±" shows degrees presenting no practical problem. The symbol "−" in the sliding forces shows that the plunger rod 6 was pushed down smoothly, "+" shows strong resistance, and "±" shows degrees of resistance presenting no practical problem.

TABLE 1

| Silicone Coating Concentration (%) | | | |
|---|---|---|---|
| Medicine Contact Section | Medicine Non-Contact Section | Degrees of Turbidity | Sliding Force |
| 0.1 | 0.1 | − | + |
| 0.3 | 0.3 | ± | + |
| 0.5 | 0.5 | + | + |
| 0.1 | 1.0 | − | ± |
| 0.1 | 2.0 | − | − |
| 0.1 | 5.0 | − | − |
| 1.0 | 1.0 | + | ± |
| 5.0 | 5.0 | + | − |

It has been found from these results of the experiment that the syringe 3 in accordance with the present invention is obtained by silicone coating the solution of medicine contact section in a concentration not exceeding 0.3% (W/V) and silicone coating the solution of medicine non-contact portion in a concentration of 1% or more (W/V), preferably in a concentration of 1-5% (W/V).

Other embodiments are shown below. (1) In the foregoing embodiment, the silicone coating concentration for the inner wall of the syringe barrel 3 contacting the solution of medicine is set to a value not exceeding 0.3% (W/V). However, where the solution of medicine is in a small quantity, hardly any obstacle substantially occurs to movement of the gaskets 4 and 5 and plunger rod 6 without the silicone coating. In other words, the concentration not exceeding 0.3% (W/V) in the claims set out hereinbefore includes 0%.

(2) Application of the syringe 3 according to the present invention is not limited by the type of solution of medicine, but covers all solutions of medicines to be freeze-dried for use.

(3) In the foregoing embodiment, the silicone oil solutions having predetermined concentrations are prepared by adding silicone oil to a liquefied gas of chlorofluorocarbon (flon) or the like. Instead of using chlorofluorocarbon, silicone oil suspended in water may be used.

Further, there is no specific limitation to silicone oil used as long as it is applicable to the syringe barrel interior, and may be dimethylpolysiloxane, cyclic polydimethylsiloxane or the like.

(4) In the foregoing embodiment, the solvent in the second chamber 3B is led to the freeze-dried powder in the first chamber 3A through the bypass passage 9 formed in the syringe barrel 3. However, the first gasket 4 itself may include a valve structure for leading the solvent in the second chamber 3B to the freeze-dried powder in the first chamber 3A when the plunger rod 6 is pushed in.

In short, any structure may be used as long as it is capable of leading the solvent in the second chamber 3B to the freeze-dried powder in the first chamber 3A when the plunger rod 6 is pushed in.

(5) The present invention of course is applicable to a syringe of a two-compartment syringe that does not include the holder 10 or stopper 14 described in the foregoing embodiment.

The shapes, materials, dimensions and the like of the needle 1, syringe 3, two gaskets 4 and 5 and plunger rod 6 are variable according to use conditions. A different embodiment will be described now.

(6) In a two-compartment syringe in this embodiment, supporting pieces 11a and 11b of the first finger hook 11 have a pair of half cylinders 13A and 13B formed integral with end faces thereof lying adjacent the opening of the syringe 3, for surrounding the flange 8. These two half cylinders 13A and 13B have half ring projections 13a and 13b formed integral with outer peripheral surfaces thereof for detachably and elastically engaging, in the axial direction of the syringe, a plastic retaining stopper 14 mounted on the plunger rod 6.

Figure 7:
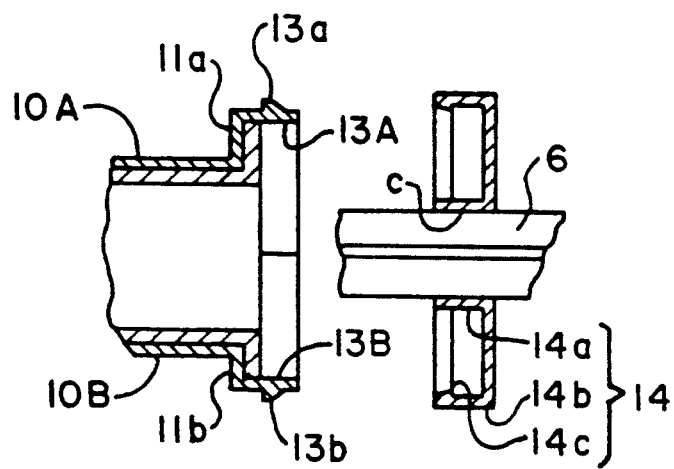
FIG. 7 is an enlarged sectional view of a principal portion showing a different embodiment of the present invention.

As shown in FIG. 7, the retaining stopper 14 includes an inner tube portion 14a having an inside diameter larger than the outside diameter of the plunger rod 6 and smaller than the outside diameter of the first gasket 4, and a syringe barrel portion 14b mounted on the half cylinders 13A and 13B of the first finger hook 11. The syringe barrel portion 14b has an annular projection 14c formed integral with an inner peripheral surface thereof for elastically engaging the half ring projections 13a and 13b.

A plug 15 of halogenobutyl rubber is inserted into the needle connecting side 2 of the syringe 3, which is perforated by the needle 1 attached to the needle connecting side 2. The inner tube portion 14a has an inner peripheral surface defining a guide surface "a" for guiding movement of the plunger rod 6 axially of the syringe 3. With the guide surface "a" thus provided, the plunger rod can be pushed in smoothly without wobbles.

Figure 8:
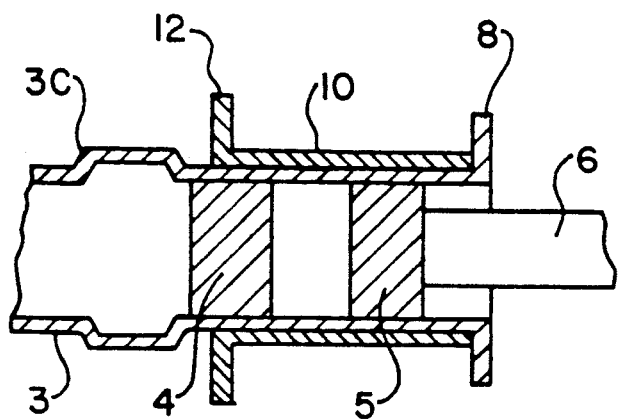
FIGS. 8 to 10 are sectional views showing further embodiments, respectively.

(7) In the construction shown in FIG. 8, the flange 8 disposed at the opening end of the syringe 3 acts also as the first finger hook 11. Of the outer peripheral surface of the syringe 3, the syringe barrel between the flange 8 and ridge 3C has a plastic holder 10 detachably attached to this syringe barrel. Further, the second finger hook 12 is formed integral with the end of the holder 10 adjacent the needle connecting side 2 of the syringe 3.

Figure 9:
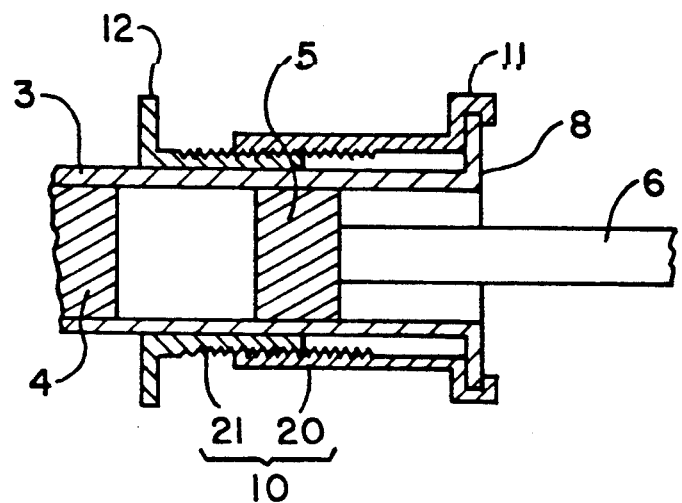

(8) In the construction shown in FIG. 9, a holder 10 is mounted peripherally of the syringe barrel 3, which includes tubular members 20 and 21 screwed to be extendible and contractible axially of the syringe 3. A first finger hook 11 is formed integral with an end of the large diameter tubular member 20 of the holder 10 for elastically engaging the flange 8 of the syringe barrel 3. Further, a second finger hook 12 is formed integral with an end of the small diameter tubular member 21 adjacent the needle connecting side 2 of the syringe 3.

Figure 10:
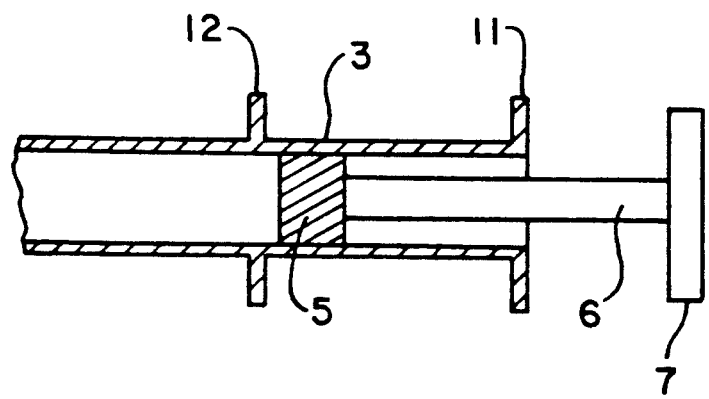

(9) In the construction shown in FIG. 10, the first finger hook 11 and second finger hook 12 are formed integral with the syringe 3. In this case, a practical advantage of low manufacturing cost is provided in that it may be assembled with a ready-made syringe and that it may be produced independently of a syringe for which a relatively high shaping precision is required.

(10) In each of the foregoing embodiments, the first finger hook 11 and second finger hook 12 are provided on the syringe barrel 3 in the same direction. These first finger hook 11 and second finger hook 12 may be arranged on the syringe barrel 3 in different direction.

(11) The shapes, materials, dimensions and the like of the syringe 3, gasket 5 and plunger rod 6 are variable according to use conditions. Further, the shapes, materials, dimensions and the like of the first finger hook 11 and second finger hook 12 are also variable according to use conditions.

Different embodiments will be described further.

Figure 11:
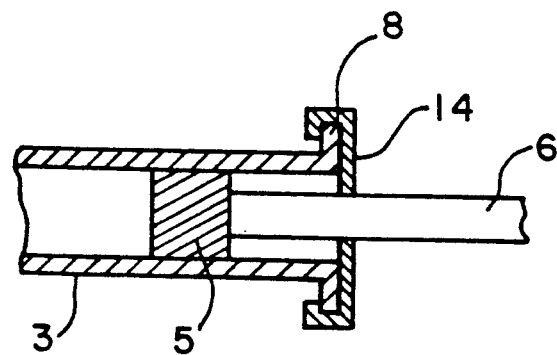
FIG. 11 is a sectional side view of a principal portion showing a further embodiment.

(12) In the construction shown in FIG. 11, a stopper 14 is mounted on the flange 8 disposed at the opening end of the barrel 3 for contacting the second gasket 5 in the axial direction of the syringe barrel 3 to prevent the second gasket 5 from moving out.

Figure 12:
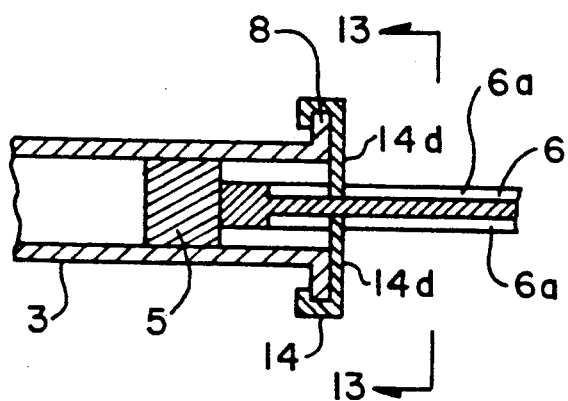
FIG. 12 is a sectional side view of a principal portion of a further embodiment.
Figure 13:
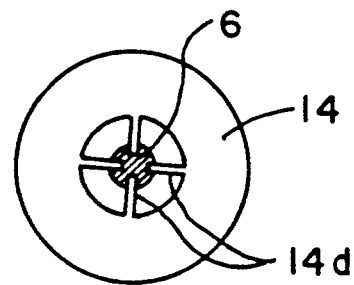
FIG. 13 is a sectional view taken on line 13—13 of FIG. 12.

(13) FIGS. 12 and 13 show a further embodiment of the present invention. The plunger rod 6 includes engaging grooves 6a defined in four peripheral positions thereof and extending axially of the syringe barrel 3. The flange 8 at the opening end of the barrel 3 has a stopper 14 mounted thereon and including four engaging projections 14d for engaging the engaging grooves 6a of the plunger rod 6, respectively. Thus, the second gasket 5 is prevented from moving out by contact between the engaging projections 14d of the stopper 14 and one ends of the engaging grooves 6a of the plunger rod 6.

Figure 14:
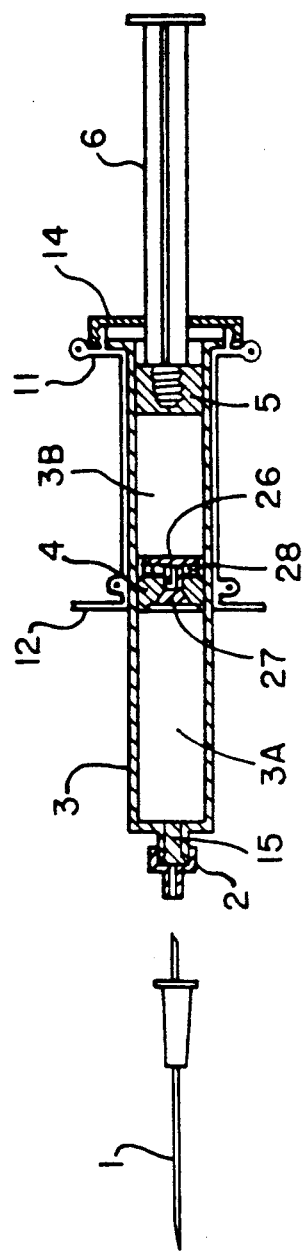
FIG. 14 is a sectional side view showing a further embodiment in a state of starting an injection.
Figure 15:
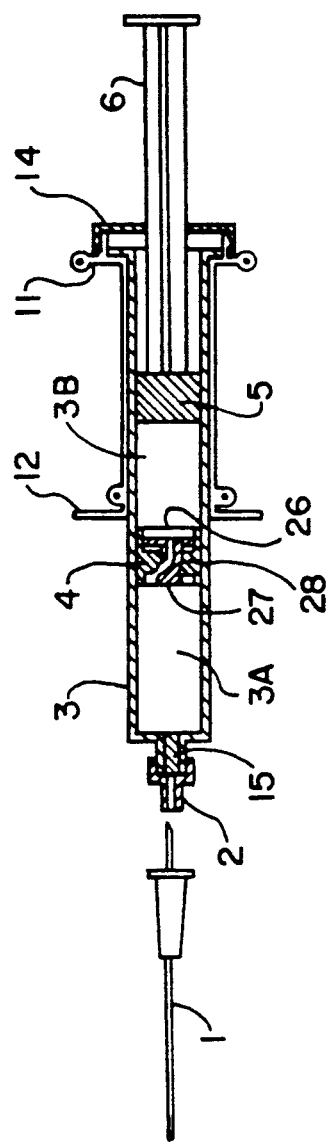
FIG. 15 is a sectional side view showing a further embodiment in a state halfway through an injection.

(14) FIGS. 14 and 15 show a further embodiment of the present invention. The first gasket 4 itself inserted into the syringe barrel 3 includes an inflow limiting structure for leading the solvent contained in the second chamber 3B into the first chamber 3A only when the plunger rod 6 is pushed in.

Specifically, the first gasket 4 includes a flow passage 26 intercommunicating the first chamber 3A and second chamber 3B, a valve 27 for closing the flow passage 26 from the side of the first chamber 3A, and a spring 28 for elastically urging the valve 27 in a closing direction. The valve 27 opens against the elastic urging force of the spring 28 when the pressure in the second chamber 3B reaches a set value as a result of a push-in operation of the plunger rod 6. As distinct from the preceding embodiments, a needle 1' attached to the syringe in this embodiment has an obtuse end and is used mainly in an injection for an affected organ during a surgical operation.

(15) In each of the foregoing embodiments, the stopper 14 is formed independently of the syringe 3. However, the stopper 14 may be formed integral with the syringe 3.

(16) The shapes, materials, dimensions and the like of the syringe 3, two gaskets 4 and 5 and plunger rod 6 are variable according to use conditions. The shape, material, dimensions and the like of the stopper 14 are also variable according to use conditions.

We claim:

1. A two-compartment syringe comprising:
   a. a barrel having a needle connecting side and an opening side;
   b. a means for attaching a needle at said needle connecting side;
   c. a first elastic gasket and a second elastic gasket, said gaskets being spaced apart and slidably contained within said barrel between said needle connecting side and said opening side, with said first gasket positioned between said second gasket and said needle connecting side and with said second gasket positioned between said first gasket and said opening side;
   d. a plunger rod attached to said second gasket;
   e. a first chamber within said barrel and between said needle attaching means and said first gasket;
   f. a second chamber within said barrel and between said first gasket and second gasket;
   g. a bypass passage in said barrel for transfer of a fluid between said second chamber and said first chamber;

h. a first coating including a first silicone oil solution formed on an inner wall of said barrel, said first silicone oil solution having a concentration no more than 0.3% (W/V) which is contacted by a solution of medicine to be freeze-dried; and i. a second coating substantially out of contact with said solution of medicine, said second coating including a second silicone oil solution having a concentration of at least 1% (W/V) and formed on an inner wall of said barrel.

2. The two-component syringe of claim 1, wherein said silicone oil solutions are prepared by dissolving silicone oil in a chlorofluorocarbon.

3. The two-compartment syringe of claim 1, wherein said needle attaching means includes a bore containing a rubber plug which can be perforated by a needle attached to said needle attaching means.

4. The two-compartment syringe of claim 1, further including a first finger hook projecting diametrically outwardly from said barrel and a second finger hook located on an intermediate portion of said barrel displaced from said first finger hook toward said needle attaching means and projecting diametrically outwardly from said barrel.

5. The two-compartment syringe of claim 4, wherein said finger hooks are formed integrally with a holder detachably mounted on said barrel.

6. The two-compartment syringe of claim 1, further including a stopper for contacting said plunger rod in an axial direction to prevent said plunger rod and said second gasket from falling out of said barrel.

7. The two-compartment syringe of claim 6, wherein said stopper includes a guide surface for guiding movement of said plunger rod axially within said barrel.

8. A two-compartment syringe comprising:
a. a barrel having a needle connecting side and an opening side;
b. a means for attaching a needle at said needle connecting side, wherein said needle attaching means is unsealed at the time a needle is attached;
c. a first elastic gasket and a second elastic gasket, said gaskets being spaced apart and slidably contained within said barrel between said needle connecting side and said opening side, wherein said first gasket is positioned between said second gasket and said needle connecting side and said second gasket is positioned between said first gasket and said opening side;
d. a plunger rod attached to said second gasket;
e. a first chamber within said barrel and between said needle attaching means and said first gasket;
f. a second chamber within said barrel and between said first gasket and second gasket;
g. a stopper inflow limiting means within said barrel for leading said fluid contained in one of said chambers to the other of said chambers only pushing in said plunger rod;
h. a stopper located at said opening side end, wherein said stopper contacts said plunger rod in an axial direction to said plunger rod and prevents said second gasket from falling out of said barrel;
i. a first finger hook at said opening side projecting diametrically outwardly of said barrel; and
j. a second finger hook located on an intermediate portion of said barrel displaced from said first finger hook toward said needle connecting side and projecting diametrically outwardly from said barrel.

9. The two-compartment syringe of claim 8, wherein said stopper includes a guide surface for guiding movement of said plunger rod axially within said barrel.

10. The two-compartment syringe of claim 9, wherein said two finger hooks are integrally formed with a holder detachably mounted on said barrel.

* * * * *

UNITED STATES PATENT AND TRADEMARK OFFICE
CERTIFICATE OF CORRECTION

PATENT NO. : 5,290,228
DATED : March 1, 1994
INVENTOR(S) : Osamu Uemura and Yukio Kusu It is certified that error appears in the above-indentified patent and that said Letters Patent is hereby corrected as shown below:

Column 7 Line 39 "inventor" should read --inventors--.

Claim 2 Line 11 Column 11 "two-component" should read --two-compartment--.

Claim 8 Line 19 Column 12 after "only" insert --upon--.

Signed and Sealed this

Twenty-eighth Day of June, 1994

Attest:

BRUCE LEHMAN

Attesting Officer    Commissioner of Patents and Trademarks